United States Patent
Morganti et al.

(10) Patent No.: US 7,186,685 B2
(45) Date of Patent: Mar. 6, 2007

(54) COMPOSITIONS COMPRISING GELATIN-GLYCINE AND CAROTENOIDS

(75) Inventors: Pierfrancesco Morganti, Aprilia (IT); Richard Lee Roberts, Johnston, IA (US)

(73) Assignee: Mavi Sud S.R.L., Aprilia Lt (IT)

( * ) Notice: Subject to any disclaimer, the term of this patent is extended or adjusted under 35 U.S.C. 154(b) by 0 days.

(21) Appl. No.: 11/177,500

(22) Filed: Jul. 11, 2005

(65) Prior Publication Data

US 2006/0009398 A1 Jan. 12, 2006

(30) Foreign Application Priority Data

Jul. 9, 2004 (EP) ............................. 04103266

(51) Int. Cl.
*C07K 14/00* (2006.01)

(52) U.S. Cl. .......................................... 514/2; 530/350

(58) Field of Classification Search .................... 514/2; 530/350

See application file for complete search history.

(56) References Cited

U.S. PATENT DOCUMENTS

| 3,206,316 A |   | 9/1965  | Klaüi |   |
|---|---|---|---|---|
| 3,655,406 A | * | 4/1972  | Klaui | ........................ 426/96 |
| 3,998,753 A | * | 12/1976 | Antoshkiw et al. | ........... 516/58 |
| 5,356,636 A | * | 10/1994 | Schneider et al. | .......... 424/489 |
| 5,733,884 A |   | 3/1998  | Barbul et al. |   |
| 6,013,250 A |   | 1/2000  | Cannell et al. |   |
| 6,756,358 B2 | * | 6/2004 | Iwamoto et al. | .............. 514/12 |

FOREIGN PATENT DOCUMENTS

EP   0197898 A1   10/1986
WO   WO 98/52165   11/1998

OTHER PUBLICATIONS

Morganti et al., The Future of Cosmetic Dermatology, J. Appl. Cosmetol., 1987, vol. 5, pp. 145-158.*
European Search Report of EP 04103266.5 (2004).

* cited by examiner

*Primary Examiner*—Karen Cochrane Carlson
(74) *Attorney, Agent, or Firm*—Nixon & Vanderhye P.C.

(57) ABSTRACT

The invention relates to cosmetic and pharmaceutical agents and compositions useful in the treatment of those phenomena and manifestations generally causing or accompanying the aging of skin, ocular tissues and other tissues. In particular the invention relates to the use of different mixture of carotenoids, preferably lutein, and gelatin-glycine for improving hydration, elasticity and lipid content of the skin and for protecting skin and ocular tissues from hazardous radiations.

17 Claims, 15 Drawing Sheets

COMPOSITIONS COMPRISING GELATIN-GLYCINE AND CAROTENOIDS

FIELD OF THE INVENTION

The invention relates to cosmetic and pharmaceutical agents and compositions useful in the treatment of those phenomena and manifestations generally causing or accompanying the aging of skin, ocular and other tissues. In particular the invention relates to the use of carotenoids or gelatin-glycine or different mixture thereof for improving hydration, elasticity and lipid content of the skin and for protecting skin and ocular tissues from hazardous radiations and retinopathy.

BACKGROUND OF THE INVENTION

Gelatin-glycine is a known product, marketed for example under the Trade name Quick Moist®, comprising a mixture of gelatin and glycine in a proportion from 2:1 to 3:1 parts by weight.

The skin hydration effect of orally administered Gelatin-glycine is reported in the prior art for instance in EP-A-197898 (P. Morganti). Also the activity of Gelatin-glycine for concomitant topical and oral administration in increasing skin surface lipids, decreasing free radicals in blood and decreasing lipid peroxides is reported in literature: P. Morganti et al.: *Cosmetic & Toiletries Magazine*, Vol. 115, No. 9, September 2000.

Other works of the same authors have recently shown that antioxidant carotenoids given as diet supplements or in a topical formulation produce a significant photo protective activity, characterized by decreasing blood free radicals and lipid peroxides and accompanied by skin hydration and skin lipid improvement. See P. Morganti et al.: *International Journal of Cosmetic Science*, Vol. 24, pp. 331–339, 2002.

Although the results reported in the prior art prove already promising, they show that the increase of gelatin-glycine effect by increasing treatment time and amounts tends to a steady-state in which no further significant improvement can be observed. For instance it is reported by Morganti et al. in *Journal of Applied Cosmetology*, Vol. 7, 1989 pp. 103–109, that augmenting the oral administration of gelatin-glycine from 4 to 6 or even 8 pills a day does not cause any significant augmentation in skin hydration or reduction in superficial facial lines. In the same way, it is observed in *Cosmetics & Toiletries*, Vol. 103, April 1988, pp. 77–80, that the values of skin hydration recorded after 60 days treatment with gelatin-glycine do not significantly differ from those obtained after 30 days treatment.

For this reason, there remains the need for more efficient active principles exhibiting an enhanced activity and still capable of causing a rising effect over the long terms.

SUMMARY OF THE INVENTION

The invention is based on the unexpected findings that antioxidant carotenoids and oxygenated carotenoids are able to strongly improve the previously reported antiaging and photo protective activity of gelatin-glycine, when administered concomitantly either in a mixture or independently.

For this reason, a first object of the present invention are mixtures of gelatin-glycine and carotenoids or oxygenated carotenoids, preferably lutein, wherein the ratio between gelatin and glycine is about 2:1 by weight and the ratio between gelatin/glycine and carotenoids or oxygenated carotenoids is from 6:1 to 10:1 by weight.

A second object of the invention are cosmetic and therapeutic compositions or diet supplements comprising these mixtures as active agent, with optional antioxidant or additive agents, and a cosmetically or therapeutically acceptable excipient.

A further object of the invention is a kit of parts for the separate administration of two active agents, wherein the one active agent comprises gelatin-glycine and the other active agent comprises carotenoids or oxygenated carotenoids, preferably lutein.

Still further objects of the invention are methods for preparing the mixtures, the compositions and the kits and the cosmetic or therapeutic use of the same for increasing skin hydration, skin elasticity, superficial skin lipids, or for decreasing lipid peroxides or for photo protection and for increasing visual activity.

The experimental results reported in the examples show the improved effect of the concomitant application of gelatin/glycine and lutein versus the effect produced by each of the two substances given alone.

DETAILED DESCRIPTION OF THE INVENTION

Figure 1:
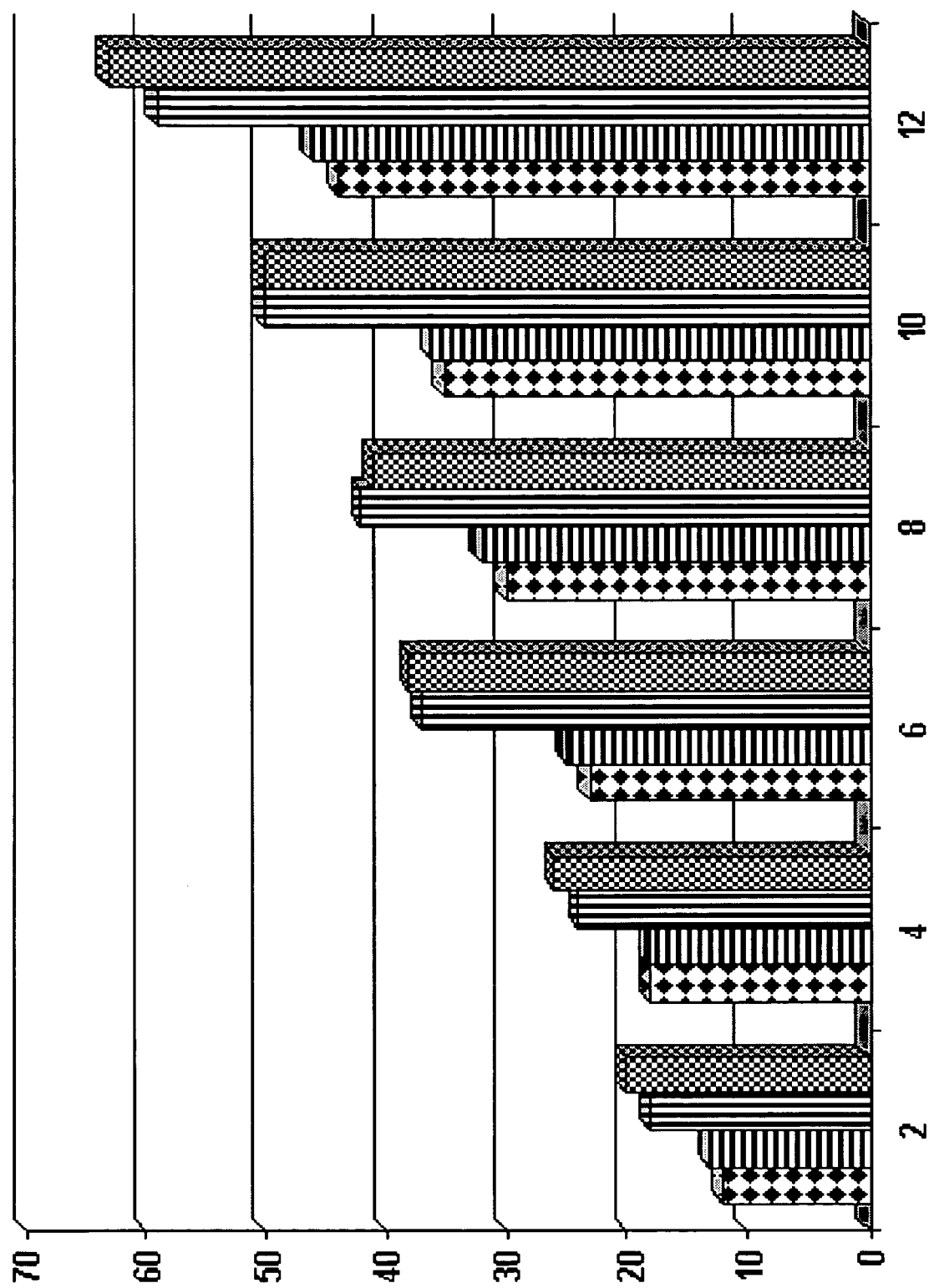
FIG. 1 illustrates the superficial skin lipids increase (percents) versus time (weeks) in healthy women affected by xerotic and sensitive skin treated twice a day both by diet supplements and topically with: group I ◘ (gel-gly diet plus placebo topical); group II ■ (lutein diet plus placebo topical); group III ▥ (gel-gly diet plus gel-gly topical); group IV ▩ (lutein diet plus lutein topical).

The oxidative stress due to the continuous exposure to solar radiation and atmospheric aggressive agents represent a hazard to the integrity of skin and other tissues resulting in their precocious aging. Aging of the skin is normally caused or accompanied by different manifestations such as decrease in skin lipids, elasticity and hydration, or increase in skin lipid peroxides. The present invention mainly provides anti-aging means.

Gelatin/glycine is a known substance disclosed by P. Morganti et Al. in EP-A-0 197 898 or in *Cosmetics & Toiletries Magazine* Vol, 115, N. 9, pp. 47–56, September 2000. When gelatin and glycine are mixed together and fused at low temperature, the resulting association shows unique characteristics unlike those that might be expected from a simple mixture of the two raw material. For this reason gelatin/glycine is considered here as a unique active substance.

Gelatin may be replaced by equivalent polypeptides such as derivatives of bovine or fish collagen or by polyglucosides such as hyaluronic acid or chitin or cellulose or derivatives thereof.

Also the glycine may be replaced by other low molecular weight amino acids, such as alanine or valine or arginine.

The ratio of gelatin to glycine is normally about 2:1 by weight, with amounts ranging from 1 to 200 mg for gelatin and 0.5 to 100 mg of glycine per unit dose, the best amount being about 24 mg gelatin and about 12 mg glycine.

Carotenoids and oxygenated carotenoids are powerful antioxidants, and they include beta-carotene, canthaxanthin, zeaxanthin, lycopen, lutein, crocetin, and capsanthin for example. Antioxidants are reported in the prior art to exhibit a protective effect against oxidative stress and lipid peroxidation. See P. Morganti et al.: *International Journal of Cosmetic Science*, Vol. 24, pp. 331–339, 2002. The preferred carotenoid according to the invention are oxygenated carotenoids and among these the very preferred one is lutein, i.e. $\beta,\epsilon$-carotene-3,3'-diol.

The ratio of gelatin/glycine to carotenoid is in ranges from about 6:1 to 10:1 by weight, preferably about 7:1. The amount for dosage unit depends on the administration way, ranging from 5 to 500 ppm, preferably from 30 to 50 ppm, for topic application unit or from 1 to 80 mg, preferably from 3 to 5 mg for systemic administration unit, for example in the form a diet integrator. When lutein is used, the best administering amounts are about 5 mg lutein concomitantly with about 36 mg gelatin/glycine.

Since carotenoids are sensitive to oxidation, their stability may be significantly improved by the use of suitable amounts of antioxidants such as vitamin C, vitamin E, lipoic acid or any other natural antioxidant substance. The preferred antioxidant is vitamin E, which may be used from 10% to 20% by weight referred to the amount of carotenoid.

The active agents according to the present invention may be formulated, singularly or together, into compositions resulting either in a systemic or in a local effect. Systemic effect is preferably obtained by oral route, although parenteral administration may also be used. For oral administration the active agents are formulated preferably into dietary or nutritional supplements. For example the composition may comprise gelatin/glycine or carotenoids or mixture thereof, together with extracts, oils, such as soy oil or others, excipients, vitamins, minerals, stabilizers, flavoring agents and any other additive for alimentation. Alternatively, soft or hard gelatin capsules, beads, particles, tablets, granulates may be used. When gelatin/glycine and carotenoid, for instance lutein, are given concomitantly in one single dosage, the carotenoid and any other additional substance are directly formulated within the soft gelatin capsules, beads, particles or tablets or are dispensed into hard gelatin capsules.

For local effect, the active agents are formulated into topical compositions for make-up also, such as a gel, a cream, a paste, a lotion, an oil etc. Any known excipient for local application may be used.

Alternatively, the active agents may be comprised within independent compositions for concomitant or subsequent use by the same or different administering ways. In this case, the gelatin/glycine and the carotenoids are formulated in a kit of parts containing two or more compositions suitable for independent administration, but intended to produce a common effect, preferably a synergistic interaction. In a preferred realization form of the invention, one composition comprises, as the sole active agent, gelatin/glycine and the other lutein, or the one composition comprises a combination of gelatin/glycine and lutein, while the other comprises gelatin/glycine alone or lutein alone, or still the one comprises the combination of both active substances and the other comprises the same combination, but intended for a different administering route. Of course, lutein is only an example of usable oxygenated carotenoid.

Normally the kit consists of an oral composition, e.g. a diet supplement, and a topical composition, e.g. a cream. When a composition comprises the combination of the two active substances, it may be replaced in the kit by two compositions each comprising one single active substance for the same administering route.

The combination of the invention or each active element of the combination are administered either topically or orally or topically and orally. When administered orally, the mixture or any single element are preferably given once or twice a day in form of a capsule, while, the topical administration are applied on clean skin twice a day in the form of a cream, a gel or a paste. The treatment may be prosecuted with progressively increasing effect over more than three months.

Figure 3:
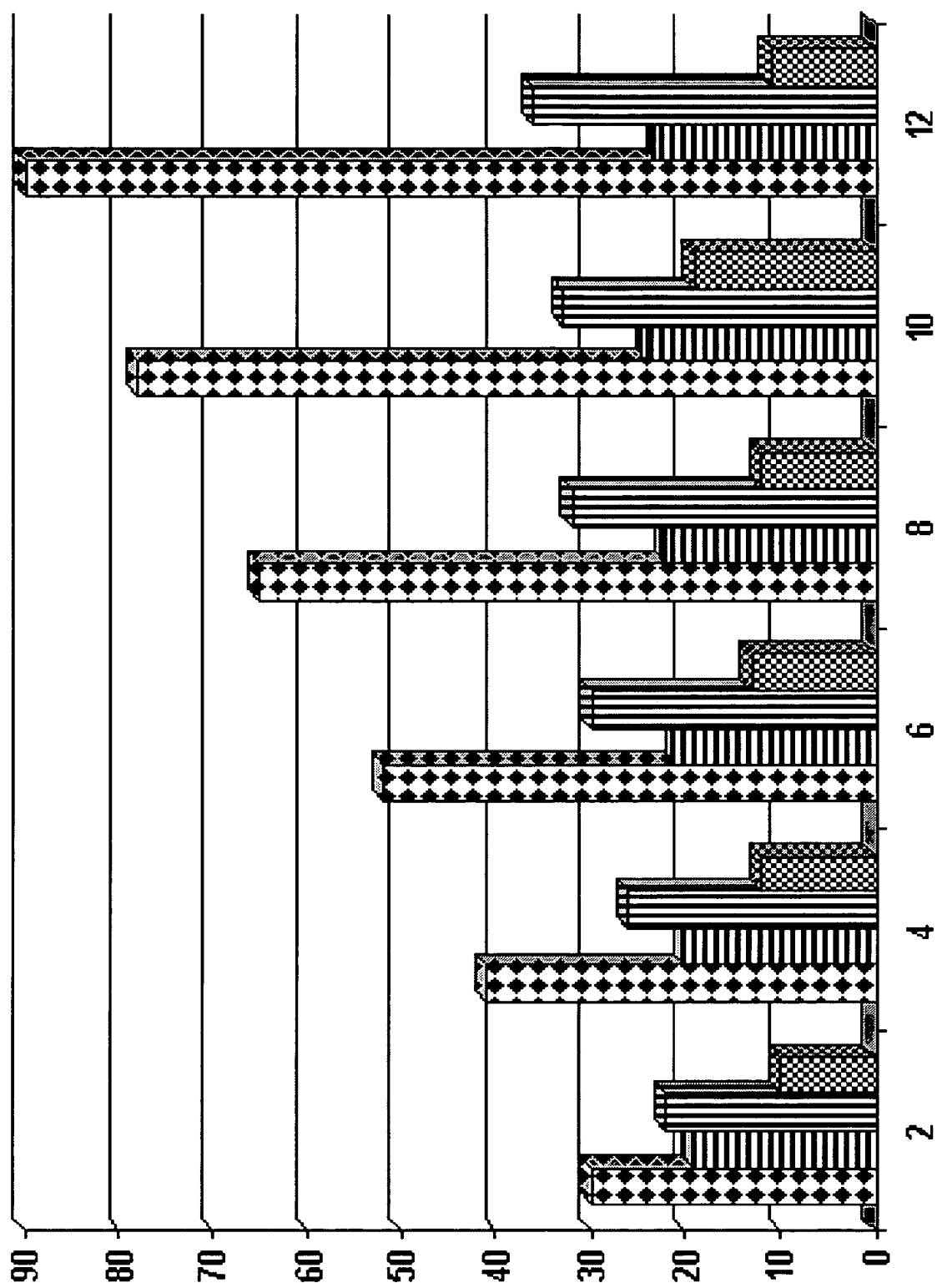
FIG. 3 illustrates the superficial skin lipids increase (percents) versus time (weeks) in healthy women treated twice a day both by diet supplements and topically with: group IX ◘ (gel-gly and lutein diet plus topical); group X ■ (placebo diet plus lutein topical); group XI ▥ (placebo diet plus gel-gly topical); group XII ▩ (placebo diet plus topical).
Figure 4:
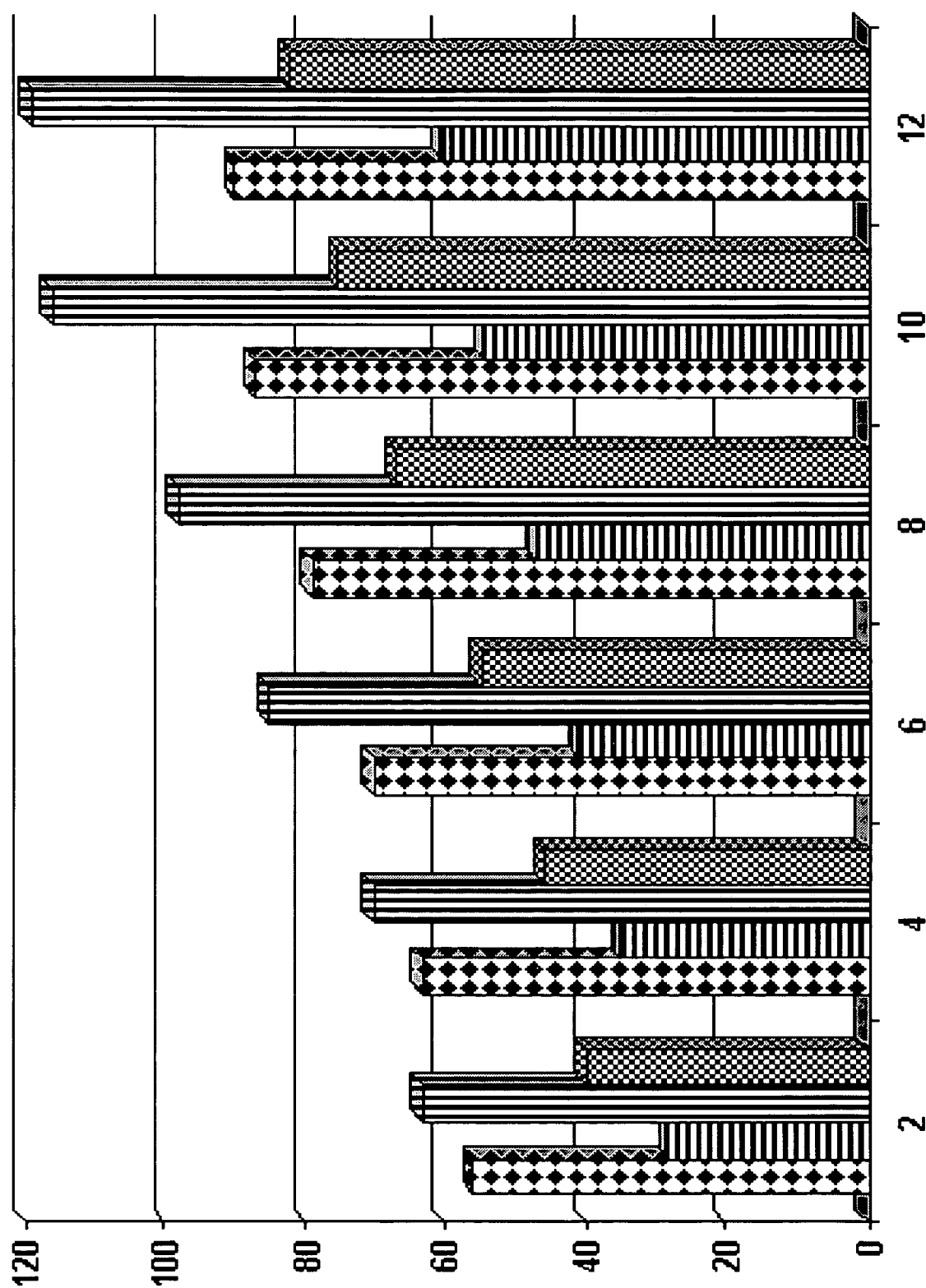
FIG. 4 illustrates the skin hydration increase (percents) versus time (weeks) in healthy women treated twice a day both by diet supplements and topically with: group ◘ (gel-gly diet plus placebo topical); group II ■ (lutein diet plus placebo topical); group III ▥ (gel-gly diet plus gel-gly topical); group IV ▩ (lutein diet plus lutein topical).
Figure 6:
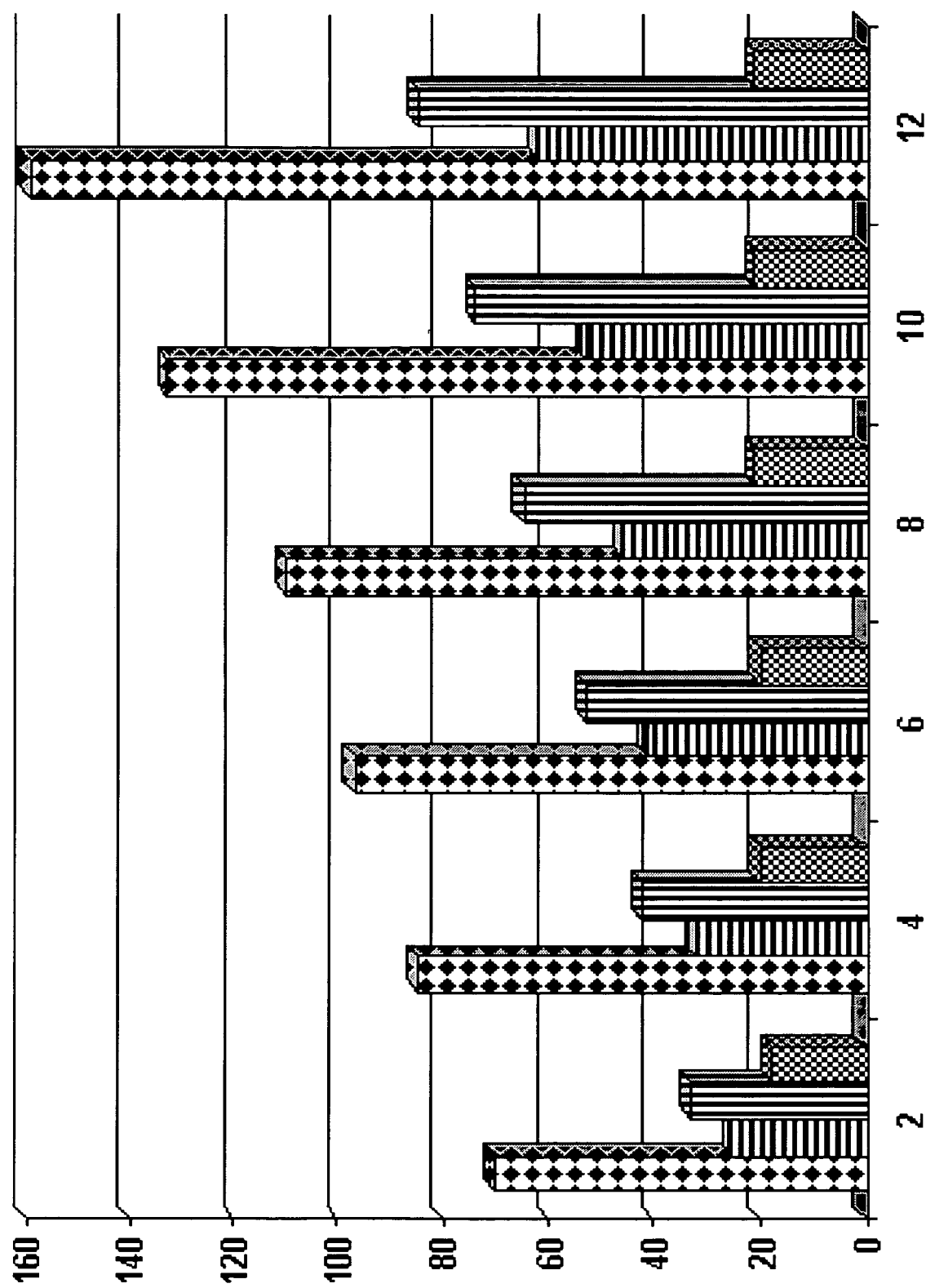
FIG. 6 illustrates the skin hydration increase (percents) versus time (weeks) in healthy women treated twice a day both by diet supplements and topically with: group IX ◘ (gel-gly and lutein diet plus topical); group X ■ (placebo diet plus lutein topical); group XI ▥(placebo diet plus gel-gly topical); group XII ▨(placebo diet plus topical).
Figure 7:
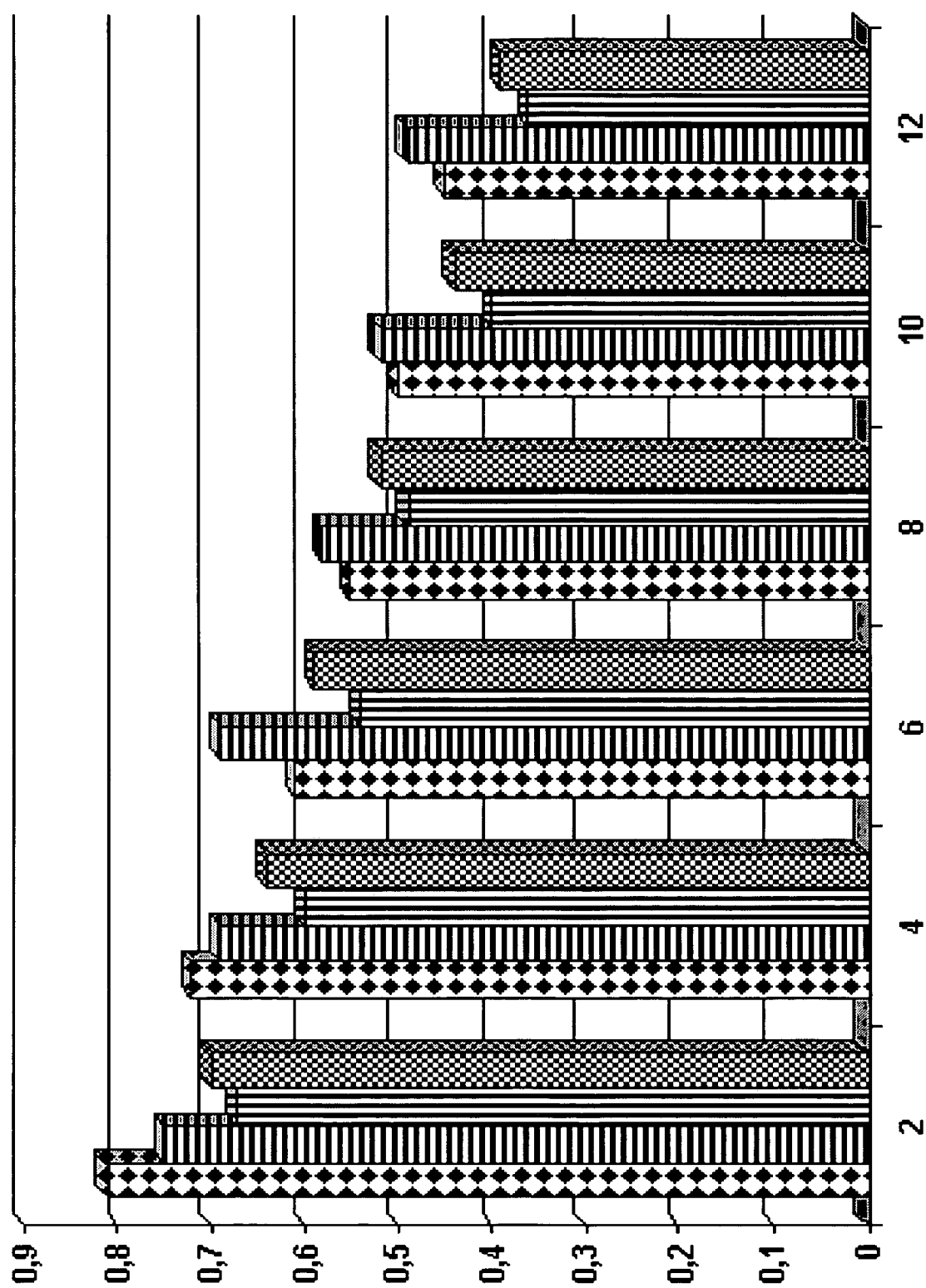
FIG. 7 illustrates the decrease of skin lipids peroxides induced by UVB light (MDA/100 mg LIPID) versus time (weeks) in healthy women treated twice a day both by diet supplements or topically with: group I ◘(gel-gly diet plus placebo topical); group II ▬(lutein diet plus placebo topical); group III ▥(gel-gly diet plus topical); group IV ▨(lutein diet plus topical).
Figure 13:
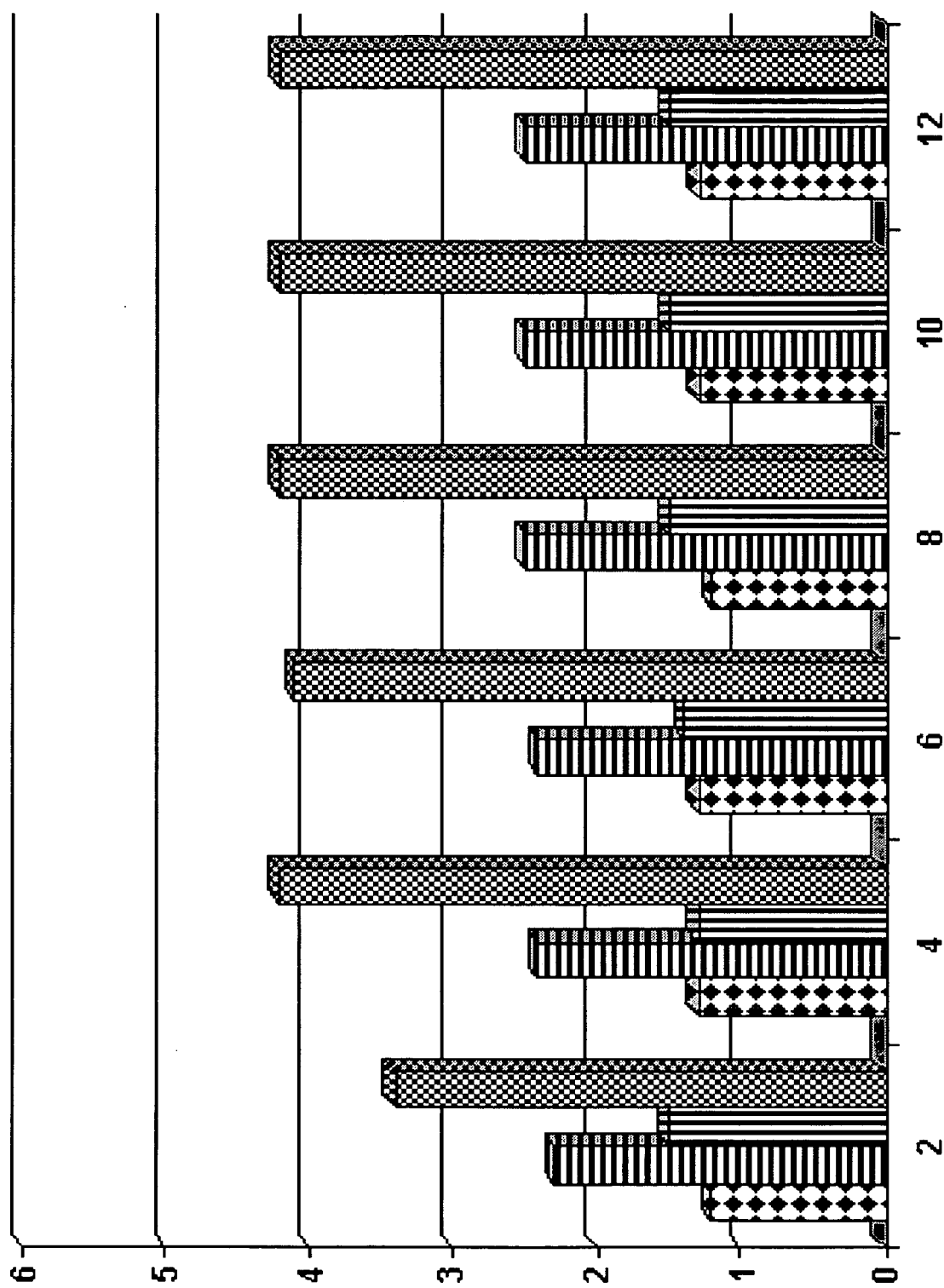
FIG. 13 illustrates the photo protective activity on forearm skin areas (SPF) versus time (weeks) in healthy women treated twice a day by diet supplements or topically with: group I ◘(gel-gly diet plus placebo topical); group II ▬(lutein diet plus placebo topical); group III ▥(gel-gly diet plus topical); group IV ▨(lutein diet plus topical).

The observed effects are the improved skin hydration (FIGS. 2 and 3), skin elasticity (FIGS. 5 and 6), and an improved content of superficial lipids (FIGS. 8 and 9) as compared to the amounts resulting from the use of any single active agents taken alone (FIGS. 1, 4 and 7). Moreover the combination exhibits a high photo protective activity capable of increasing the SPF factor of any solar protective cream (FIGS. 14 and 15), and also resulting in a reduced amount of lipid peroxides induced by UVB light (80 mj/cm$^2$/2 min) (FIGS. 8 and 9) as compared to the corresponding effects caused by any single active agent (FIGS. 7 and 13). Visual activity is also increased by the combinations of active agents of the invention. No undesirable side effect has been observed.

Experimental Section

All types of effects have been monitored according to methods known in the art. The skin hydration and the superficial lipids have been measured on face and neck skin using the 3C System (A. Cardillo et al. *J. Appl. Cosmetol.*, Vol 12. p11, 1994; G. Fabrizi et al. in "Medicina Estetica, Metodologie Diagnostiche, Preventive e Correttive" Ed. Salus International Rome, Italy, pp. 703–716, 1998). The cutaneous peroxides have been measured following the MDA method with thiobarbituric acid on woman forearm skin, which had been previously irradiated (80 mj/cm$^2$) for a week (Ohkido M, et al. *Curr. Prob. Dermatol.* Vol 10, pp. 269–278, 1980).

The skin elasticity has been evaluated, on the right forearm, using Dermaflex® A and comparing the relative elastic retraction index (RER) of the treated skin with the RER of the untreated skin (right forearm versus left forearms) on five predetermined areas marked with a proper marking pen (Gniadecka M. et al.—Suction Chamber Method For Measurement Of Skin Mechanical Properties: The Dermaflex—in "*Non-invasive methods and the skin* (Serup J and Jemec GBE Eds. CRC Press, Boca Raton, USA) p. 329–340) (1994)

The photo protective activity was monitored on other five adjacent areas of the same right forearm, pretreated with UV (80 mJ/cm$^2$). The tonality of the skin color was checked and measured 24 hours after irradiation using the Cromameter CR-300. The basic tonality of the skin color of each subject had been measured at the beginning of the trials, and stored in the colorimeter memory. All the measurements have been carried out at the controlled relative humidity (CRH) of 50%, and temperature of 22° C. and represent the average result of three measurements on the same skin area used to check the basic tonality of skin color.

Skin lipids have been evaluated according to the 3C System described by P. Morganti et al. in *Intern. J. of Appl. Cosmetol.* 24: 336 (2002) "Role of topical and nutritional supplement and oxidative stress".

Briefly, skin lipids, absorbed by a special frosted plastic foil (1 cm$^2$), were measured photometrically (and expressed as μg/cm$^2$). Determinations are based on photometric measurement of light transmission through a skin surface imprint obtained applying to the designed skin area the frosted plastic foil. It allows adherence of skin lipids in a 1 cm$^2$ area. The obtained results are reported in FIGS. 2 and 3.

Examples: For anyone of the five biological effects studied in the present experimental work, 120 voluntary women, 25 to 45 year-old and belonging to the photo type III and IV have been divided into 12 groups (group I to XII) of 10 persons. Each person received, in double blind, three tubes containing 100 gr topical product and labeled either a or b or c or d and 3 phials containing 60 capsules as diet supplement labeled either A or B or C or D. The study groups and the type of treatment for each group is reported in table I below.

Groups I to IV (40 persons) were given either gel-gly alone or lutein alone according to different administration schedules.

Groups V to VIII (40 persons) were given the combination of the invention, thus both gel-gly and lutein according to different administration schedules.

Groups IX to XII (40 persons) are given either the combination of the invention (group IX) or gel-gly plus placebo or lutein plus placebo or placebo alone.

TABLE 1

| GROUP | ORAL | TOPICAL | DOSING FREQUENCY | TEST TO BE CONDUCTED |
| --- | --- | --- | --- | --- |
| Group I | Gel-Gly | Placebo Control to skin (face and/or forearm) | Twice daily (oral and topical) | a. skin lipids<br>b. skin peroxide content<br>c. skin hydration<br>d. skin elasticity<br>e. photoprotective activity |
| Group II | Lutein 5 mg | Placebo Control to skin (face and/or forearm) | Twice daily (oral and topical) | a. skin lipids<br>b. skin peroxide content<br>c. skin hydration<br>d. skin elasticity<br>e. photoprotective activity |
| Group III | Gel-Gly | Gel-Gly | Twice daily (oral and topical) | a. skin lipids<br>b. skin peroxide content<br>c. skin hydration<br>d. skin elasticity<br>e. photoprotective activity |
| Group IV | Lutein 5 mg | Lutein 50 ppm | Twice daily (oral and topical) | a. skin lipids<br>b. skin peroxide content<br>c. skin skin hydration<br>d. skin elasticity<br>e. photoprotective activity |
| Group V | Gel-Gly | Lutein 50 ppm | Twice daily (oral and topical) | a. skin lipids<br>b. skin peroxide content<br>c. skin hydration<br>d. skin elasticity<br>e. photoprotective activity |
| Group VI | Lutein 5 mg | Gel-Gly | Twice daily (oral and topical) | a. skin lipids<br>b. skin peroxide content<br>c. skin hydration<br>d. skin elasticity<br>e. photoprotective activity |
| Group VII | Gel-Gly + Lutein 5 mg | Gel-Gly | Twice daily (oral and topical) | a. skin lipids<br>b. skin peroxide content<br>c. skin hydration<br>d. skin elasticity<br>e. photoprotective activity |
| Group VIII | Gel-Gly + Lutein 5 mg | Lutein 50 ppm | Twice daily (oral and topical) | a. skin lipids<br>b. skin peroxide content<br>c. skin hydration<br>d. skin elasticity<br>e. photoprotective activity |
| Group IX | Gel-Gly + Lutein 5 mg | Gel-Gly + Lutein 50 ppm | Twice daily (oral and topical) | a. skin lipids<br>b. skin peroxide content<br>c. skin hydration<br>d. skin elasticity<br>e. photoprotective activity |
| Group X | | 50 ppm | Twice daily (oral and topical) | a. skin lipids<br>b. skin peroxide content<br>c. skin hydration<br>d. skin elasticity<br>e. photoprotective activity |
| Group XI | | | Twice daily (oral and topical) | a. skin lipids<br>b. skin peroxide content<br>c. skin hydration<br>d. skin elasticity<br>e. photoprotective activity |
| Group XII | Placebo | Placebo | Twice daily (oral and topical) | a. skin lipids<br>b. skin peroxide content<br>c. skin hydration<br>d. skin elasticity<br>e. photoprotective activity |

The tests have been carried out under the following conditions. The topical product has been applied by lightly massaging twice a day (morning and evening) on the face, neck and right arm skin, previously cleaned with Keraidroschiuma®. The left arm was kept untreated and considered the term of comparison. Any subject received enough topical product and enough diet supplement to carry out the treatment for three months.

The diet supplement was administrated orally twice a day during main meals. Each subject has been put on Mediterranean diet with a controlled intake of carotenoids from fruits and vegetables.

All the persons were subjected to control, with clinical methods, of the serum carotenoid levels during the two weeks preceding the beginning of the treatment, during the three months treatment (every 15 days) and one month after the end of treatment (last week of the month).

All the subjects voluntary participated at the project and the experimental project has been allowed by the ethic commission.

The results of the experimental work are illustrated in FIGS. 1 to 15.

In FIG. 1, Group I versus Group II is not significant, Groups I and II versus groups III and IV are highly significant ($p<0.005$); Group III versus group IV is not significant.

Figure 2:
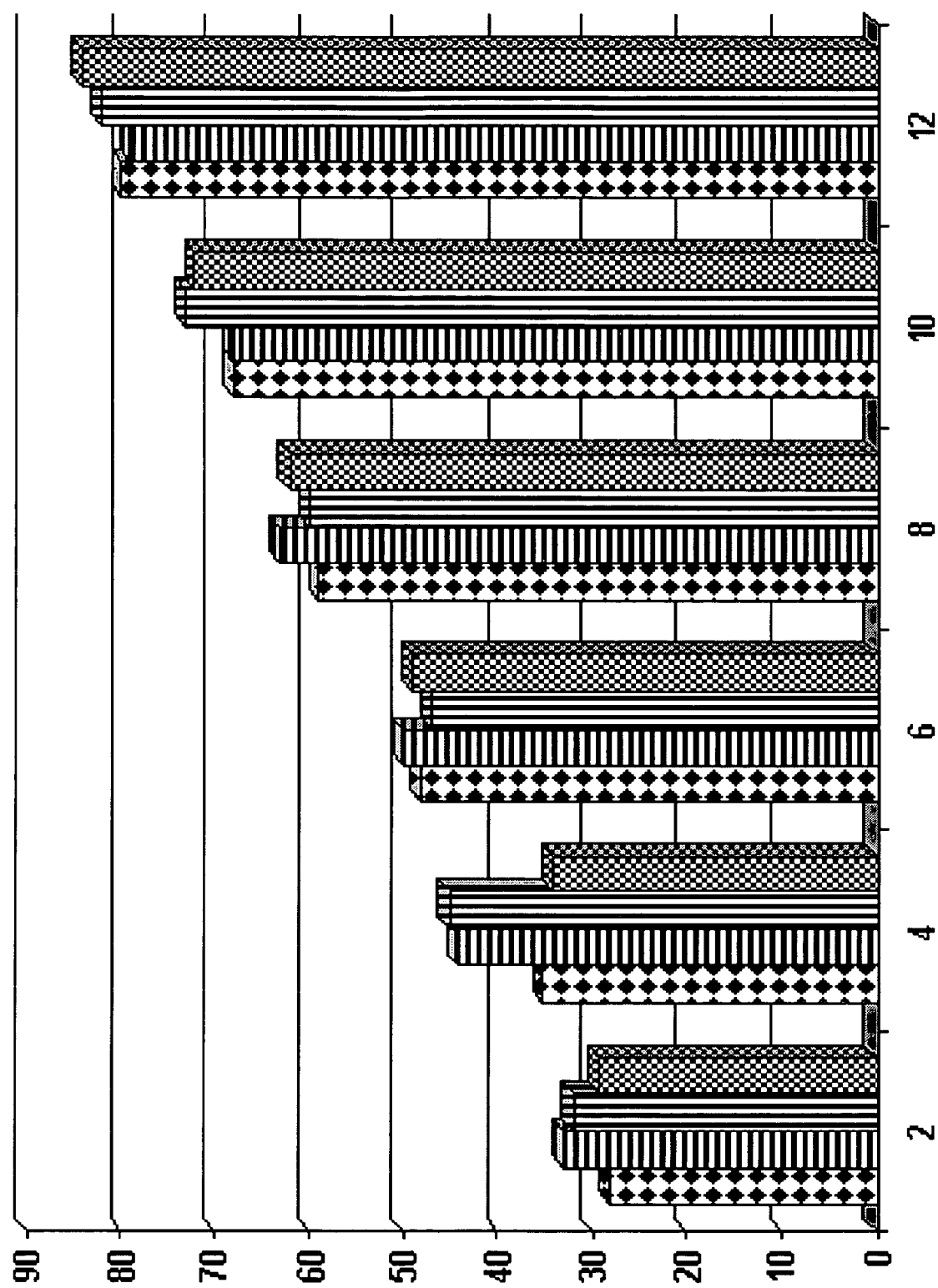
FIG. 2 illustrates the superficial skin lipids increase (percents) versus time (weeks) in healthy women treated twice a day both by diet supplements and topically with: group V ◘ (gel-gly diet plus lutein topical); group VI ■ (lutein diet plus gel-gly topical); group VII ▥ (gel-gly and lutein diet plus gel-gly topical); group VIII ▩ (gel-gly and lutein diet plus lutein topical).

In FIG. 2, all p values are significant for each week as baseline ($p<0.05$) but not significant as to group.

In FIG. 3 Group IX is highly significant vs. Groups X, XI, XII ($p<0.005$); Group XI is significant versus Groups X and XII ($p<0.05$) and highly significant versus Group XII ($p<0.005$).

In FIG. 4, Group I is highly significant versus Groups II and IV ($p<0.005$); Group I is significant versus Group III from week 6 ($p<0.05$).

Figure 5:
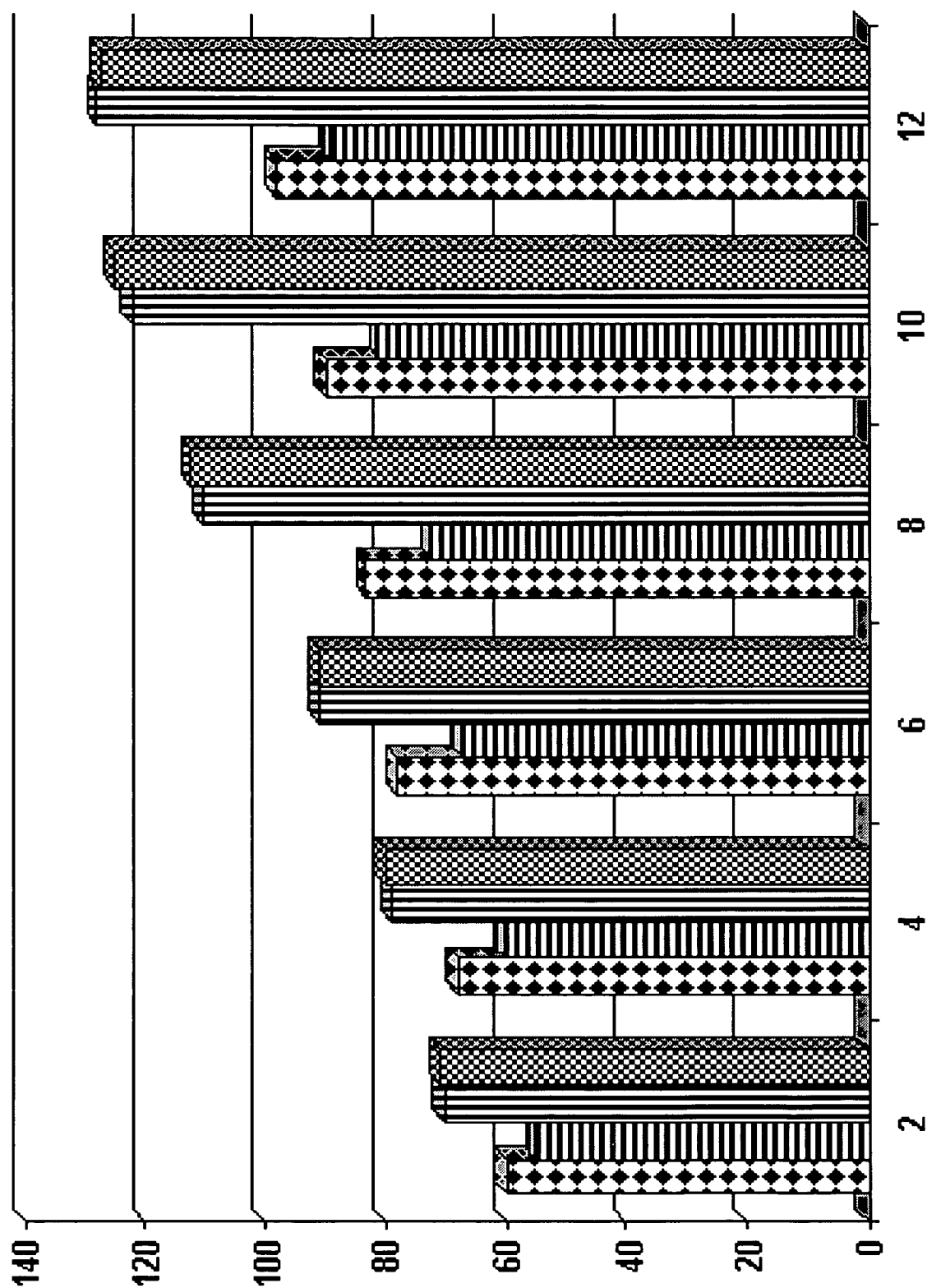
FIG. 5 illustrates the skin hydration increase (percents) versus time (weeks) in healthy women treated twice a day both by diet supplements and topically with: group V ◘ (gel-gly diet plus lutein topical); group VI ■ (lutein diet plus gel-gly topical); group VII ▥ (gel-gly and lutein diet plus gel-gly topical); group VIII ▩ (gel-gly and lutein diet plus lutein topical).

In FIG. 5, all p values are highly significant for each week as baseline ($<0.005$); Group V versus Group VI is not significant; Group VI versus Groups VII and VIII ($p<0.05$); Group VII versus Group VIII is not significant; Group V versus Groups VI, VII and VIII ($p<0.05$).

In FIG. 6, Group IX versus X, XI, XII is highly significant ($p<0.005$); Groups X and XII versus Group XI are highly significant ($p<0.005$).

In FIG. 7 Group I versus III and IV is highly significant for all the weeks ($p<0.005$); Group I versus II is not significant; Group II versus III is significant ($p<0.05$).

Figure 8:
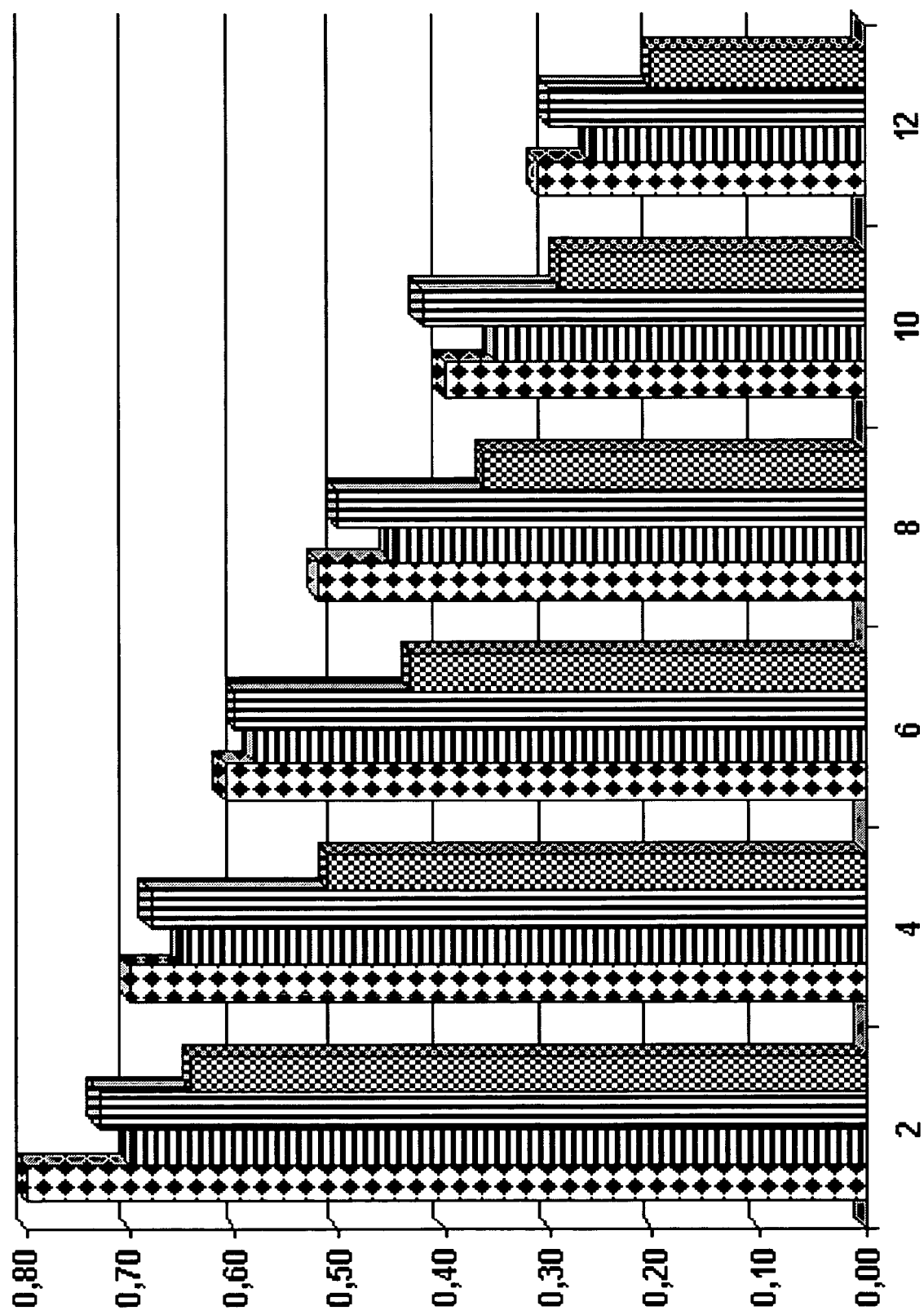
FIG. 8 illustrates the decrease of skin lipids peroxides induced by UVB light (MDA/100 mg LIPID) versus time (weeks) in healthy women treated twice a day both by diet supplements or topically with: group V ◘(gel-gly diet plus lutein topical); group VI ▬(lutein diet plus gel-gly topical); group VII ▥(gel-gly and lutein diet plus gel-gly topical); group VIII ▨(gel-gly and lutein diet plus lutein topical).

In FIG. 8, Group V versus VI is significant ($p<0.05$) and highly significant versus Group VIII ($p<0.005$); Group V versus VII is not significant.

Figure 9:
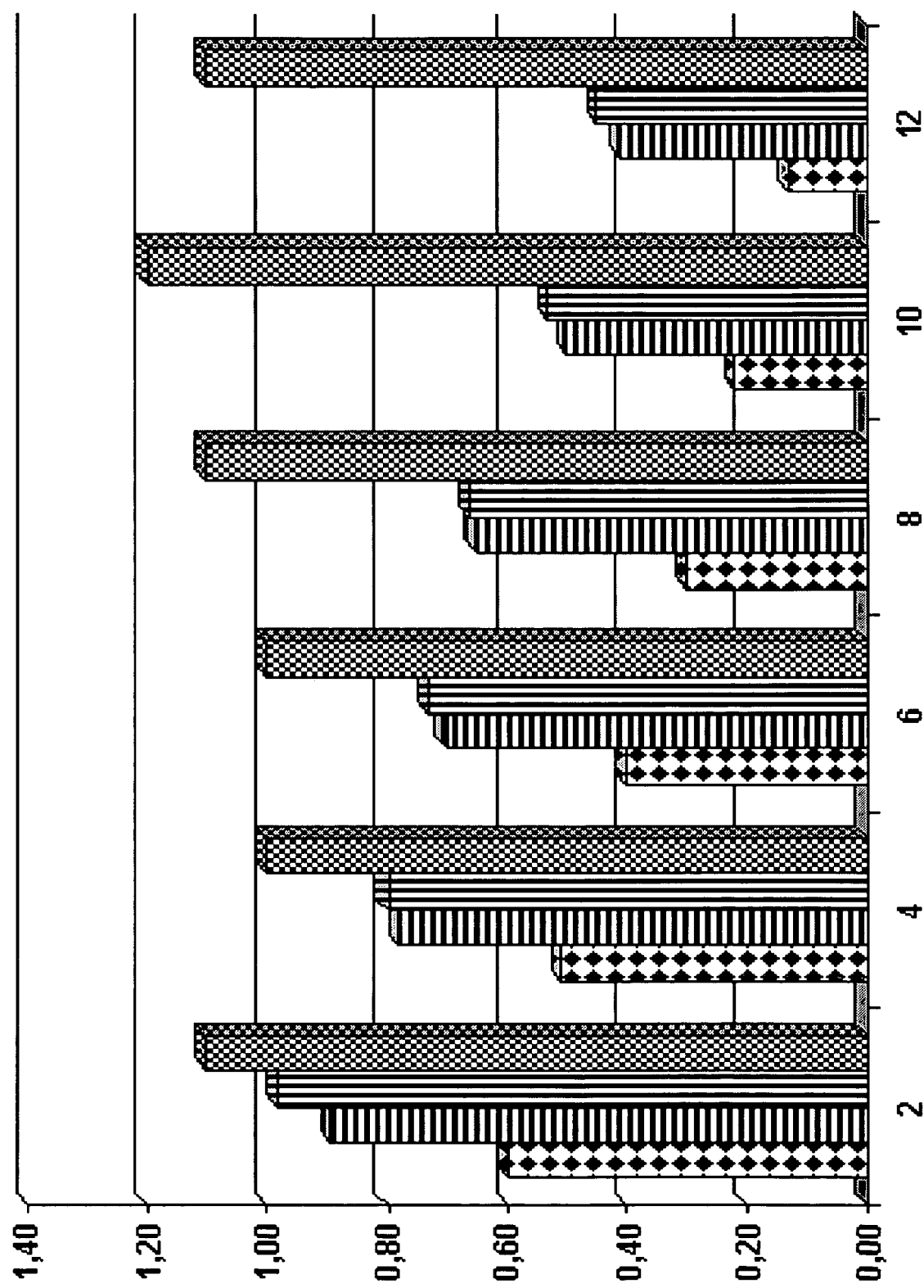
FIG. 9 illustrates the decrease of skin lipids peroxides induced by UVB light (MDA/100 mg LIPID) versus time (weeks) in healthy women treated twice a day both by diet supplements or topically with: group IX ◘(gel-gly and lutein diet plus topical); group X ▬(placebo diet plus lutein topical); group XI ▥(placebo diet plus gel-gly topical); group XII ▨(placebo diet plus topical).

In FIG. 9, Group IX versus Groups X, XI, and XII are highly significant for all the weeks ($p<0.005$); Groups X and XI versus XII are highly significant ($p<0.005$); Group X versus XI is not significant.

Figure 10:
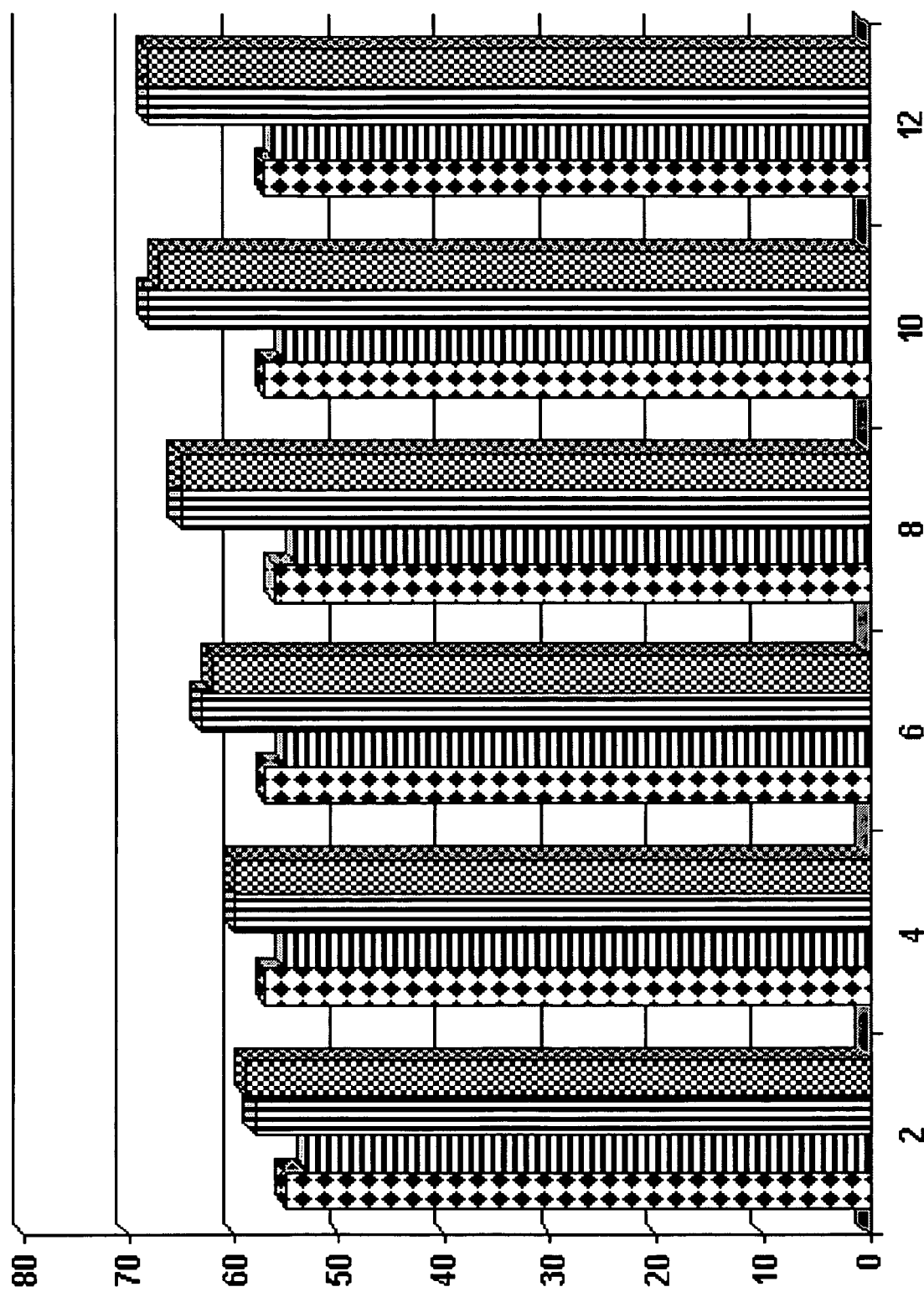
FIG. 10 illustrates the skin elasticity increase on volar forearm values (percents of penetration) versus time (weeks) in healthy women treated twice a day by diet supplements or topically with: group I ◘(gel-gly diet plus placebo topical); group II ▬(lutein diet plus placebo topical); group III ▥(gel-gly diet plus topical); group IV ▨(lutein diet plus topical).

In FIG. 10, Group I versus II is not significant; Group III versus IV is not significant; Groups I and II versus III, IV are significant ($p<0.05$) from week 6.

Figure 11:
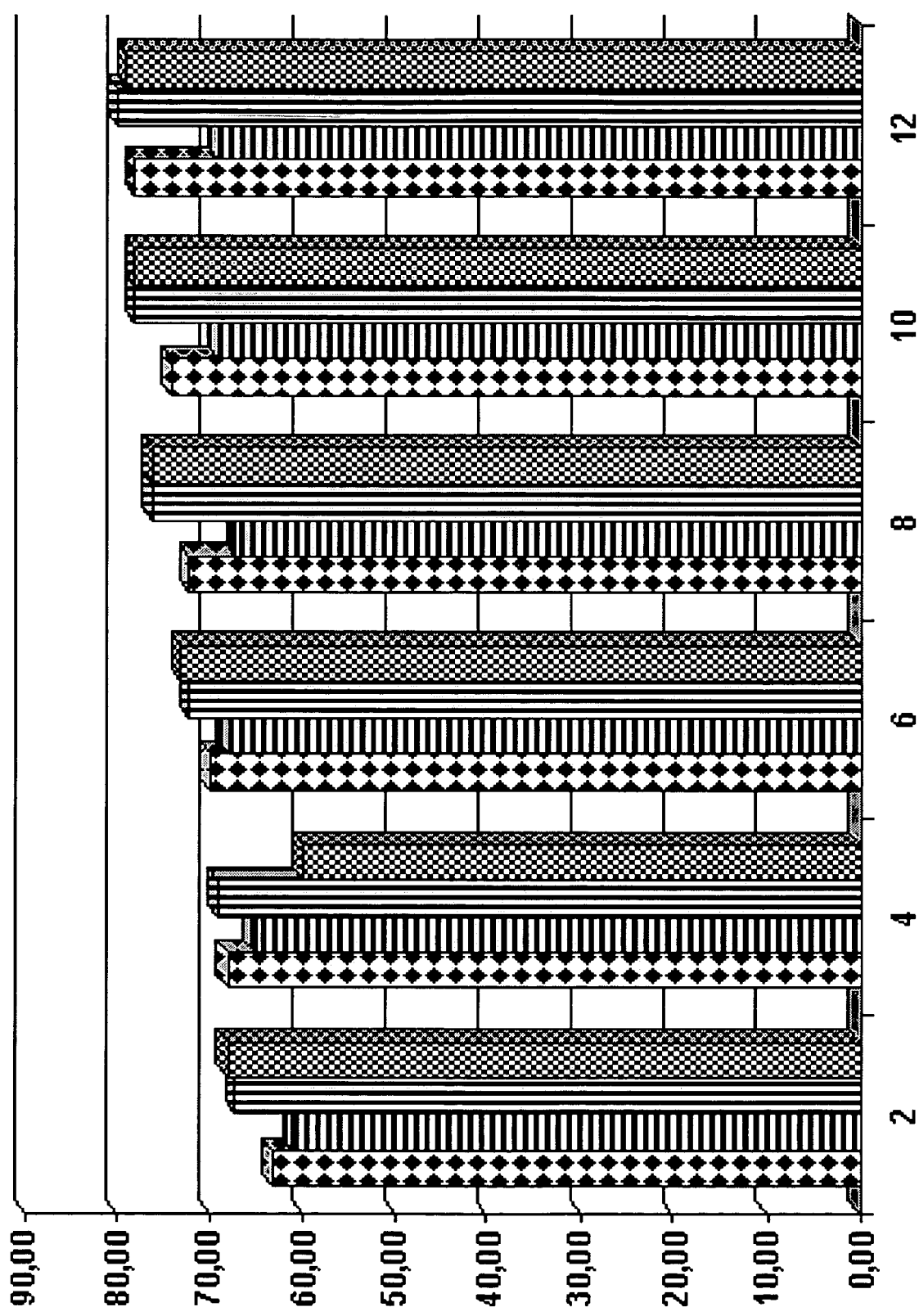
FIG. 11 illustrates the skin elasticity on volar forearm values (percents of penetration) versus time (weeks) in healthy women treated twice a day both by diet supplements or topically with: group V ◘(gel-gly diet plus lutein topical); group VI ▬(lutein diet plus gel-gly topical); group VII ▥(gel-gly and lutein diet plus gel-gly topical); group VIII ▨(gel-gly and lutein diet plus lutein topical).

In FIG. 11, Group V versus VI is significant from week 8 ($p<0.05$); Group VI versus VII, VIII is significant from week 8 ($p<0.05$).

Figure 12:
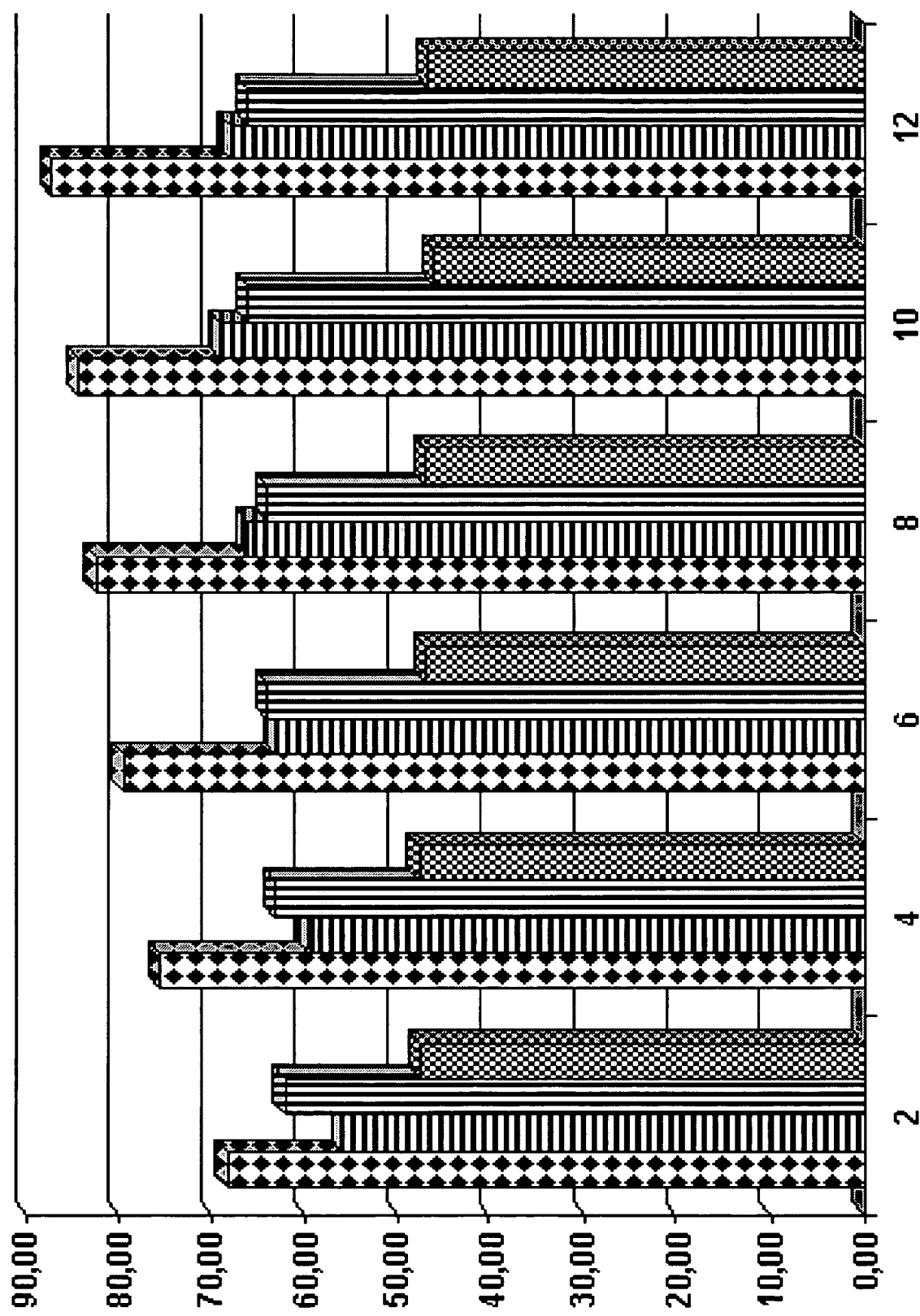
FIG. 12 illustrates the skin elasticity on volar forearm values (percents of penetration) versus time (weeks) in healthy women treated twice a day both by diet supplements or topically with: group IX ◘(gel-gly and lutein diet plus topical); group X ▬(placebo diet plus lutein topical); group XI ▥(placebo diet plus gel-gly topical); group XII ▨(placebo diet plus topical).

In FIG. 12, Group IX versus X, XI and XII is highly significant ($p<0.005$) for all the weeks; Group X versus XII is highly significant ($p<0.005$) for all the weeks; Group X versus XI is not significant.

In FIG. 13, Group I versus III is not significant; Group I versus II, IV is highly significant ($p<0.005$); Groups V and VI versus VII are highly significant ($p<0.005$); Groups V and VI versus VIII are not significant.

Figure 14:
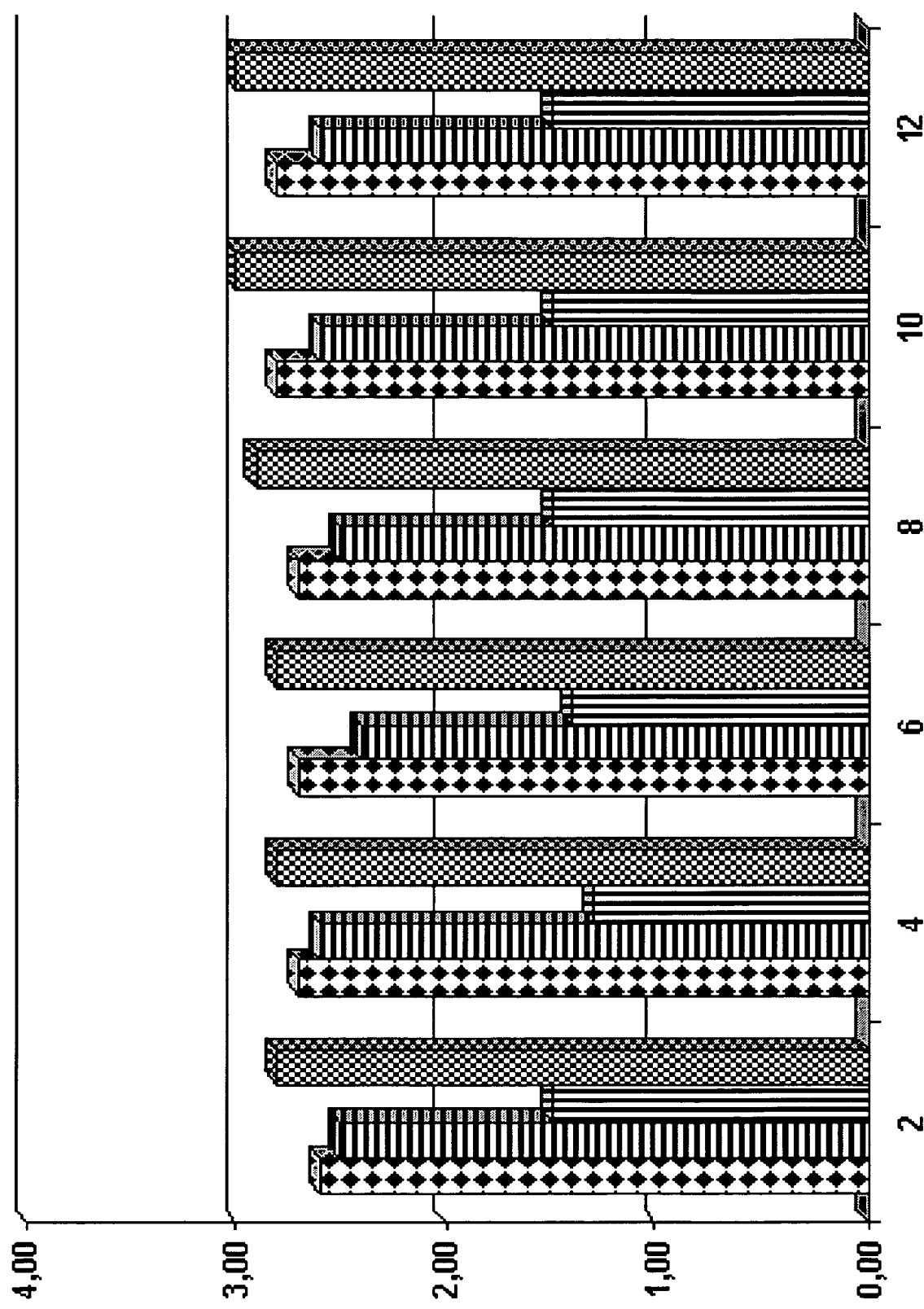
FIG. 14 illustrates the photo protective activity on forearm skin areas (SPF) versus time (weeks) in healthy women treated twice a day by diet supplements or topically with: group V ◘(gel-gly diet plus lutein topical); group VI ▬(lutein diet plus gel-gly topical); group VII ▥(gel-gly and lutein diet plus gel-gly topical); group VIII ▨(gel-gly and lutein diet plus lutein topical).

In FIG. 14, all p values of group IX are highly significant ($p<0.005$) for each week versus all the other groups; Group X versus XII is significant ($p<0.05$); Group X versus XI is not significant.

Figure 15:
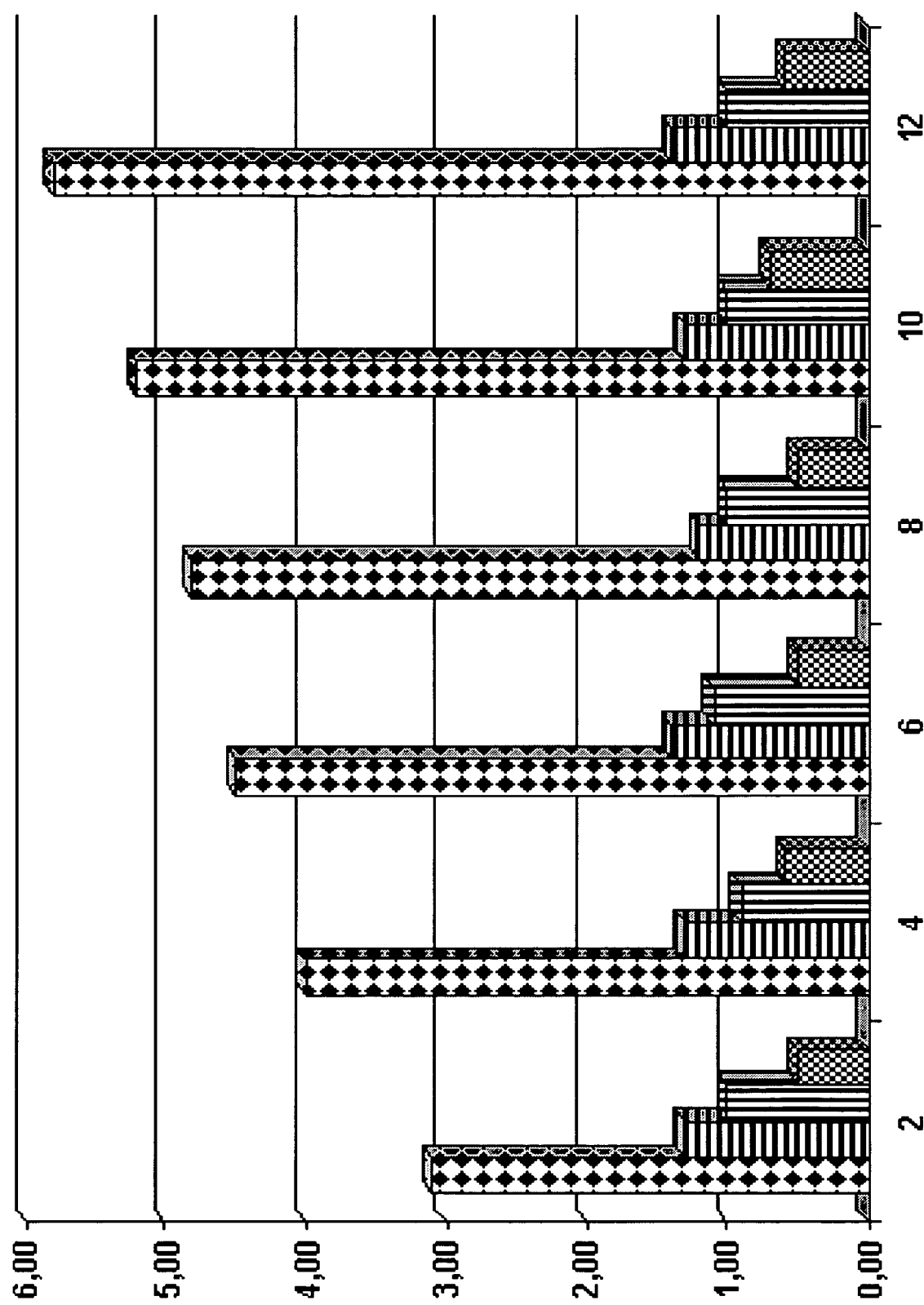
FIG. 15 illustrates the photo protective activity on forearm skin areas (SPF) versus time (weeks) in healthy women treated twice a day by diet supplements or topically with: group IX ◘(gel-gly and lutein diet plus topical); group X ▬(placebo diet plus lutein topical); group XI ▥(placebo diet plus gel-gly topical); group XII ▨(placebo diet plus topical).

In FIG. 15, Group IX versus Groups X, XI and XII is highly significant.

The invention claimed is:

1. A kit of parts for the separate administration of first and second active agents, wherein the first active agent comprises an amount of gelatin-glycine and the second active agent comprises an amount of carotpnoids or oxygenated carotenoids, wherein the ratio between gelatin and glycine is about 2:1 by weight and the ratio between gelatin/glycine and carotenoids or oxygenated carotenoids is from 6:1 to 10:1 by weight, the amount of gelatin is from 1 to 200 mg per dose, the amount of glycine is from 0.5 to 100 mg per dose, and the amount of carotenoids or oxygenated carotenoids is from 1 to 80 mg per dose for oral administration or from 5 to 500 ppm per dose for topical administration.

2. The kit of parts according to claim 1, wherein the active agents are not in the same administration form.

3. The kit of parts according to claim 2, wherein the active agents are independently each in a topical composition or in an oral composition.

4. The kit of parts according to claim 1, wherein the second agent is lutein.

5. The kit of parts according to claim 1, wherein the active agents are in two separate compositions for the same administration way.

6. A mixture of gelatin-glycine and carotenoids or oxygenated carotenoids, wherein the ratio between gelatin and glycine is about 2:1 by weight and the ratio between gelatin-glycine and carotenoids or oxygenated carotenoids is from 6:1 to 10:1 by weight, the amount of gelatin is from 1 to 200 mg per dose, the amount of glycine is from 0.5 to 100 mg per dose, and the amount of carotenoids or oxygenated carotenoids is from 1 to 80 mg per dose for oral administration or from 5 to 500 ppm per dose for topical administration.

7. The mixture of claim 6, wherein the second agent is lutein.

8. A composition comprising the mixture of claim 7 as active agent, a therapeutically or cosmetically acceptable excipient and optionally antioxidant agents.

9. The composition according to claim 8 formulated for oral or topical administration.

10. A dietary supplement comprising the mixture according to claim 7.

11. A method for preparing the mixture of claim 6, comprising mixing suitable amounts of gelatin-glycine, and optionally antioxidant agents and additive agents.

12. A method for preparing the composition according to claim 8 comprising formulating suitable amounts of gelatin-glycine, carotenoids and/or oxygenated carotenoids with a cosmetically or pharmaceutically acceptable excipient and optionally antioxidant agents and additive agents.

13. A method for preparing the kit according to claim 1 comprising packaging together compositions independently comprising the first active agent and the second active agent.

14. A method for increasing skin hydration, skin elasticity and superficial skin lipids comprising separately administering to a person the agents of the kit according to claim 1.

15. A method for decreasing lipid peroxides and/or for increasing visual activity comprising separately administering to a person the agents of the kit according to claim 1.

16. A method for increasing skin hydration, skin elasticity and superficial skin lipids comprising administering to a person the composition of claim 8.

17. A method for decreasing lipid peroxides and/or for increasing visual activity comprising administering to a person the composition of claim 8.

* * * * *